(12) United States Patent
Rush et al.

(10) Patent No.: US 6,916,159 B2
(45) Date of Patent: Jul. 12, 2005

(54) DEVICE AND METHOD EMPLOYING SHAPE MEMORY ALLOY

(75) Inventors: Benjamin M. Rush, Oakland, CA (US); Christopher V. Reggiardo, Castro Valley, CA (US)

(73) Assignee: TheraSense, Inc., Alameda, CA (US)

( * ) Notice: Subject to any disclaimer, the term of this patent is extended or adjusted under 35 U.S.C. 154(b) by 0 days.

(21) Appl. No.: 10/683,659

(22) Filed: Oct. 9, 2003

(65) Prior Publication Data

US 2004/0115067 A1 Jun. 17, 2004

Related U.S. Application Data

(60) Provisional application No. 60/424,613, filed on Nov. 6, 2002, provisional application No. 60/424,414, filed on Nov. 6, 2002, and provisional application No. 60/417,464, filed on Oct. 9, 2002.

(51) Int. Cl.[7] .............................. F04B 17/00; F04B 17/04
(52) U.S. Cl. .................... 417/321; 417/410.1; 417/416; 417/417
(58) Field of Search ............................. 417/321, 410.1, 417/416, 417

(56) References Cited

U.S. PATENT DOCUMENTS

| | | | |
|---|---|---|---|
| 4,018,547 A | * | 4/1977 | Rogen .......................... 417/321 |
| 4,439,197 A | | 3/1984 | Honda et al. |
| 4,984,581 A | | 1/1991 | Stice |
| 5,079,920 A | | 1/1992 | Whitehead et al. |
| 5,207,666 A | | 5/1993 | Idriss et al. |
| 5,211,371 A | * | 5/1993 | Coffee ........................... 251/11 |
| 5,366,292 A | | 11/1994 | Voss |
| 5,622,413 A | | 4/1997 | Kim et al. |
| 5,622,482 A | * | 4/1997 | Lee ............................. 417/321 |
| 6,059,546 A | | 5/2000 | Brenan et al. |
| 6,085,871 A | * | 7/2000 | Karamata ..................... 184/75 |
| 6,375,638 B2 | | 4/2002 | Nason et al. |
| 6,425,829 B1 | | 7/2002 | Julien |
| 6,471,980 B2 | | 10/2002 | Sirhan et al. |
| 6,669,669 B2 | | 12/2003 | Flaherty et al. |
| 6,723,072 B2 | | 4/2004 | Flaherty et al. |
| 2002/0118090 A1 | | 8/2002 | Park et al. |
| 2003/0198558 A1 | | 10/2003 | Nason et al. |

* cited by examiner

*Primary Examiner*—Cheryl Tyler
*Assistant Examiner*—Timothy P. Solak
(74) *Attorney, Agent, or Firm*—Parsons Hsue & de Runtz LLP

(57) ABSTRACT

A system for the metering and delivery of small discrete volumes of liquid is comprised of a small or minimal number of inexpensive components. One such component is a movable member, such as a miniature precision reciprocating displacement pump head, which is driven by an actuator that comprises a shape memory alloy material. The operating mechanism of the system is of little or minimal complexity. The system facilitates the precise metering and delivery of the small discrete volumes of liquid. Potential applications for the system include subcutaneous, long-term, automated drug delivery, for example, the delivery of insulin to a person with diabetes. In such an application, the small, simple and inexpensive nature of the invention would allow for its use as both a portable and a disposable system.

48 Claims, 10 Drawing Sheets

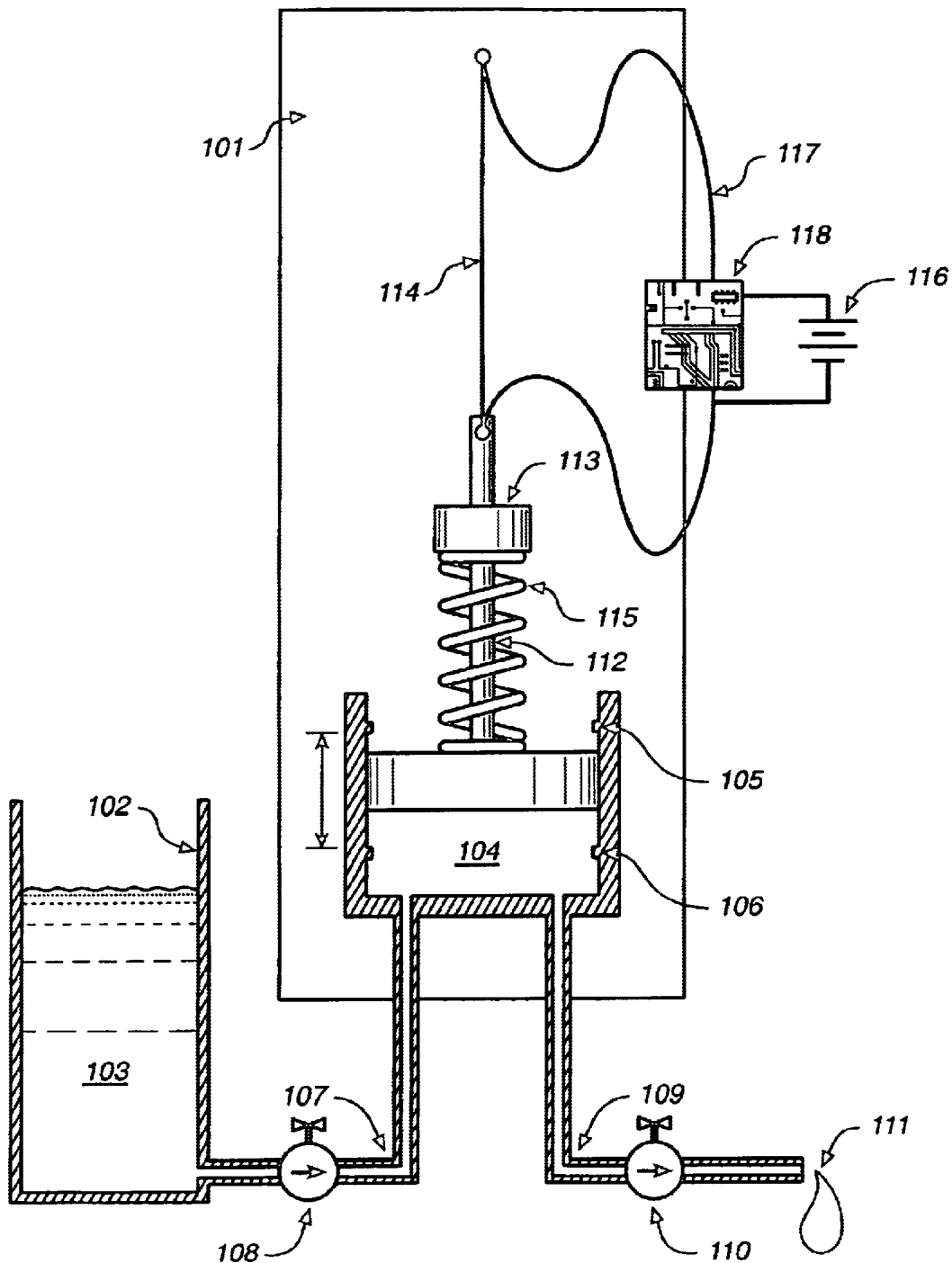
FIG._1A

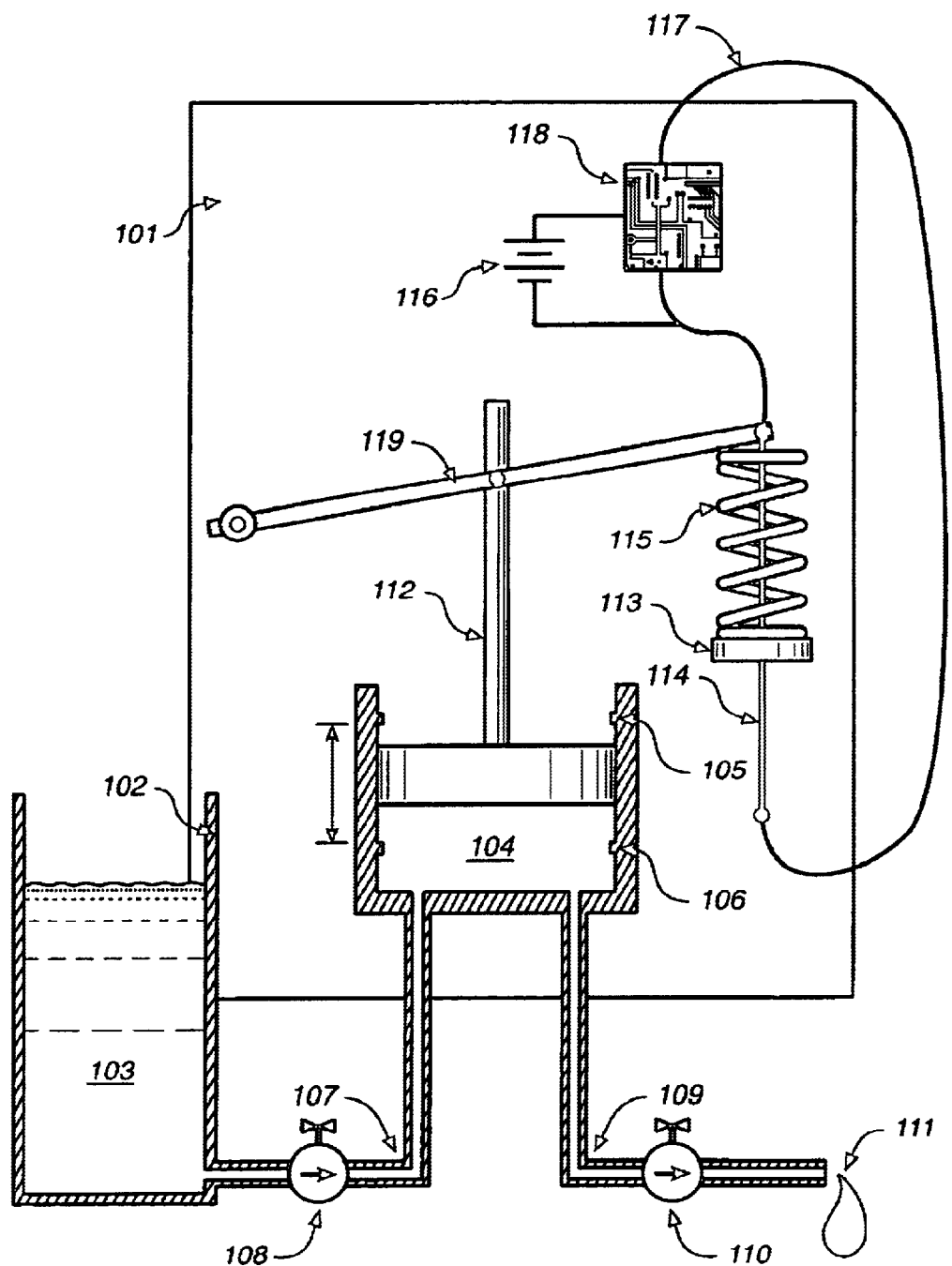
FIG._1B

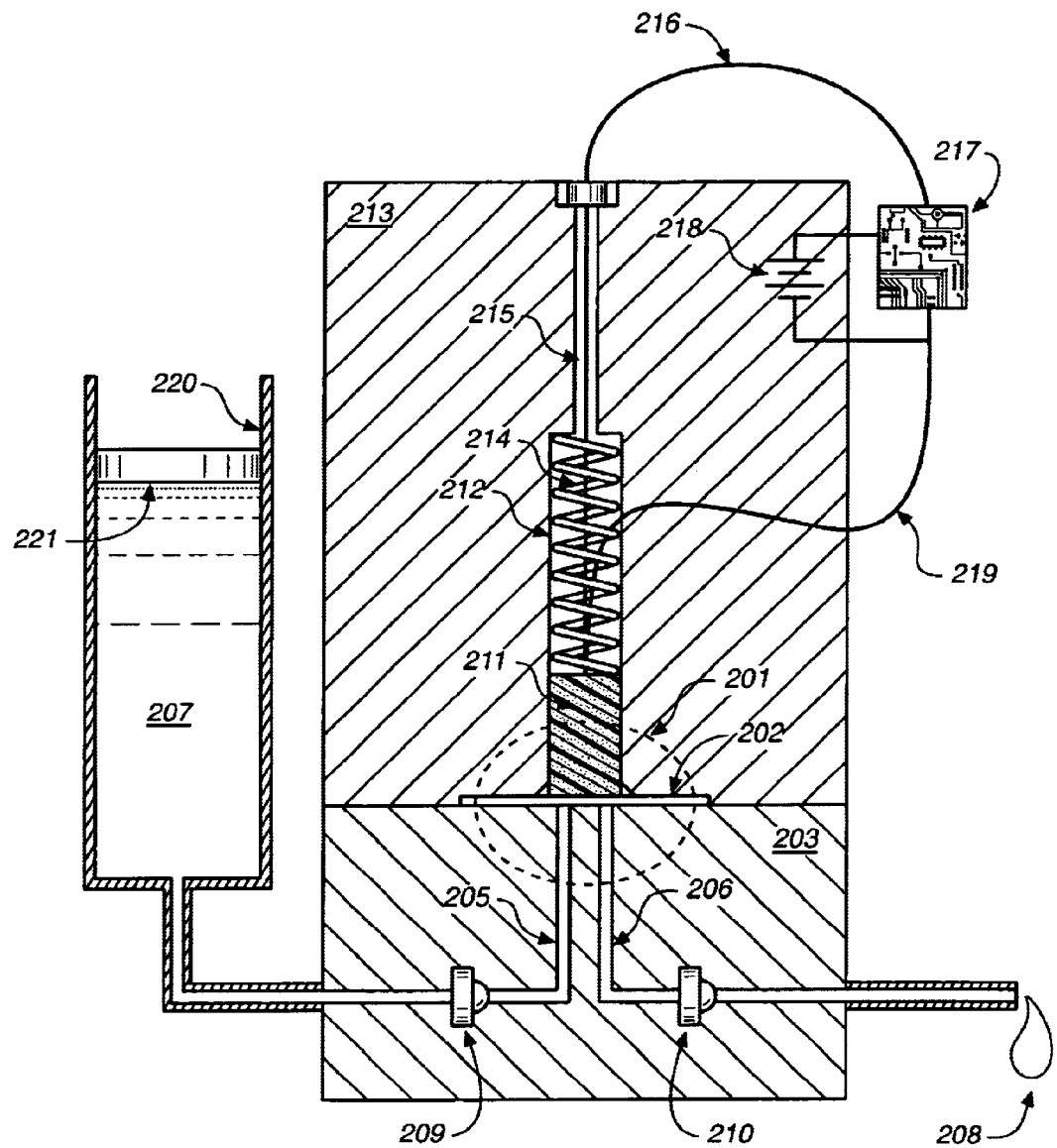
FIG._2A minimum volume
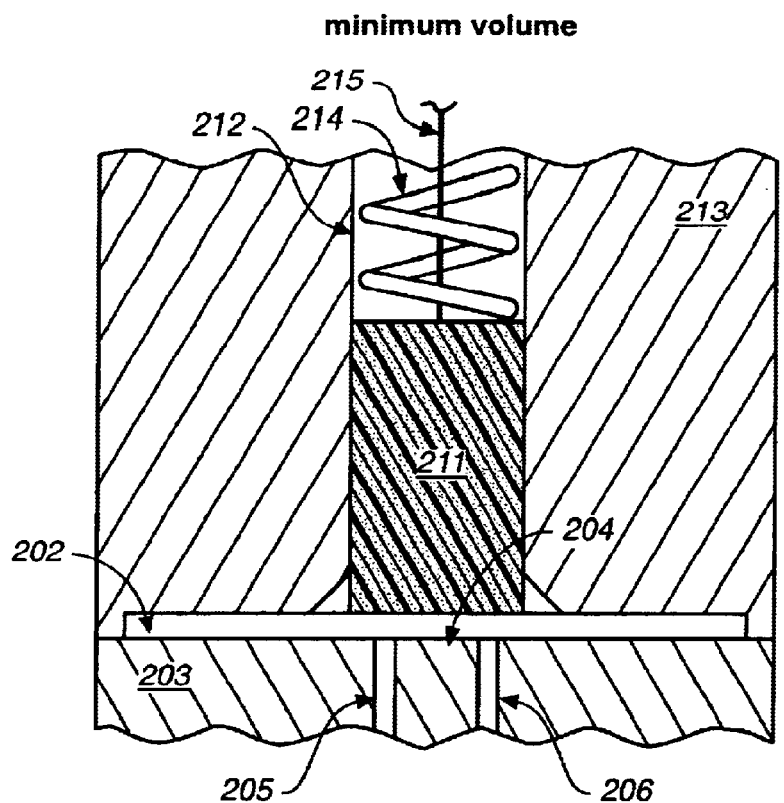
FIG._2B
maximum volume
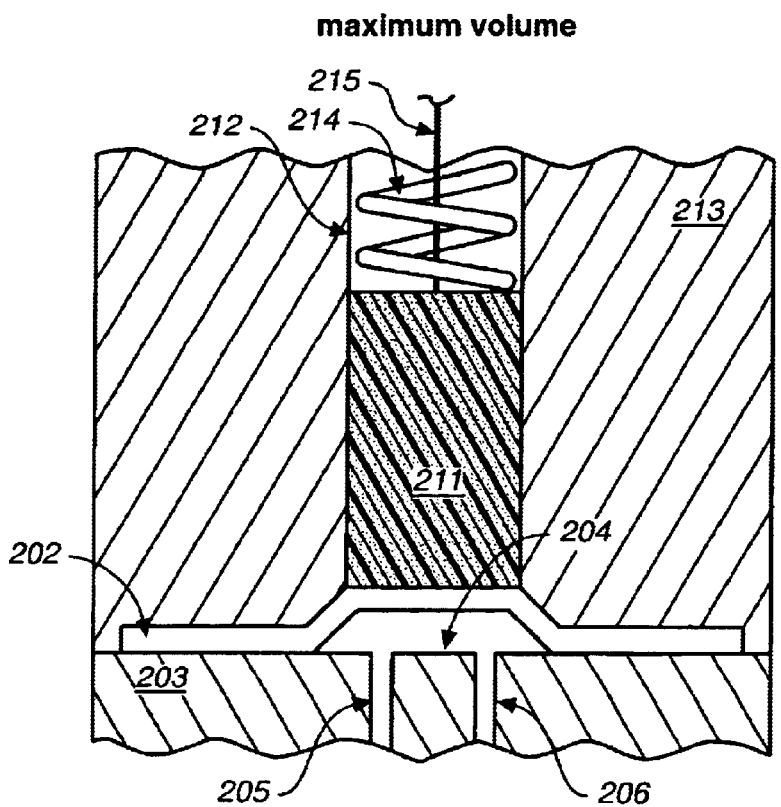
FIG._2C

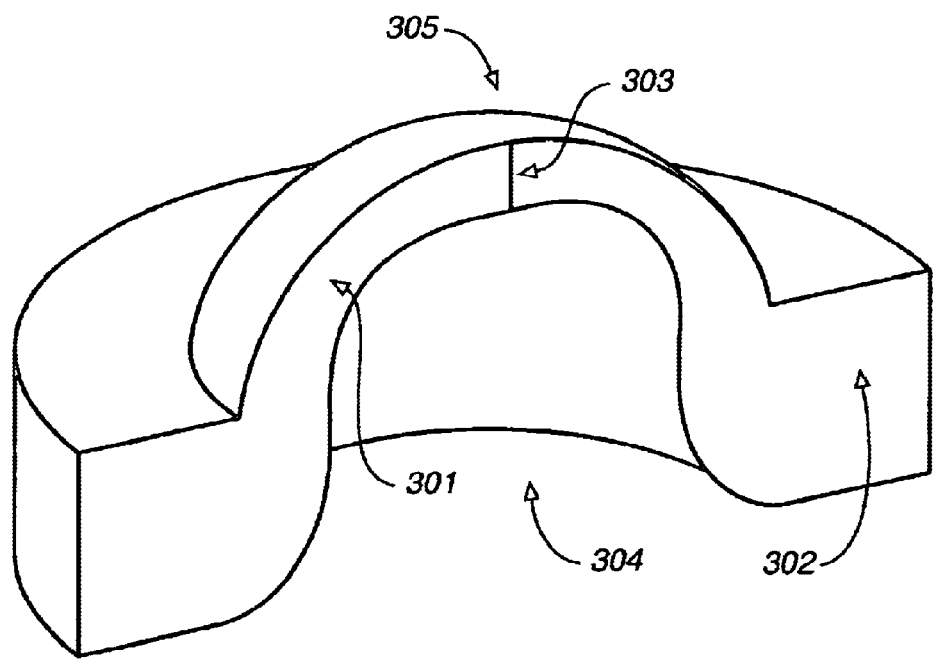
FIG._3
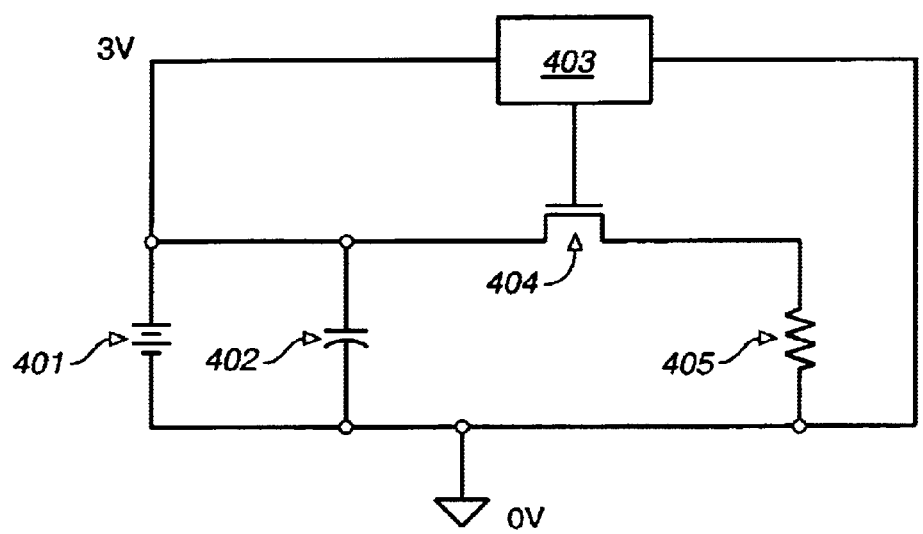
FIG._4

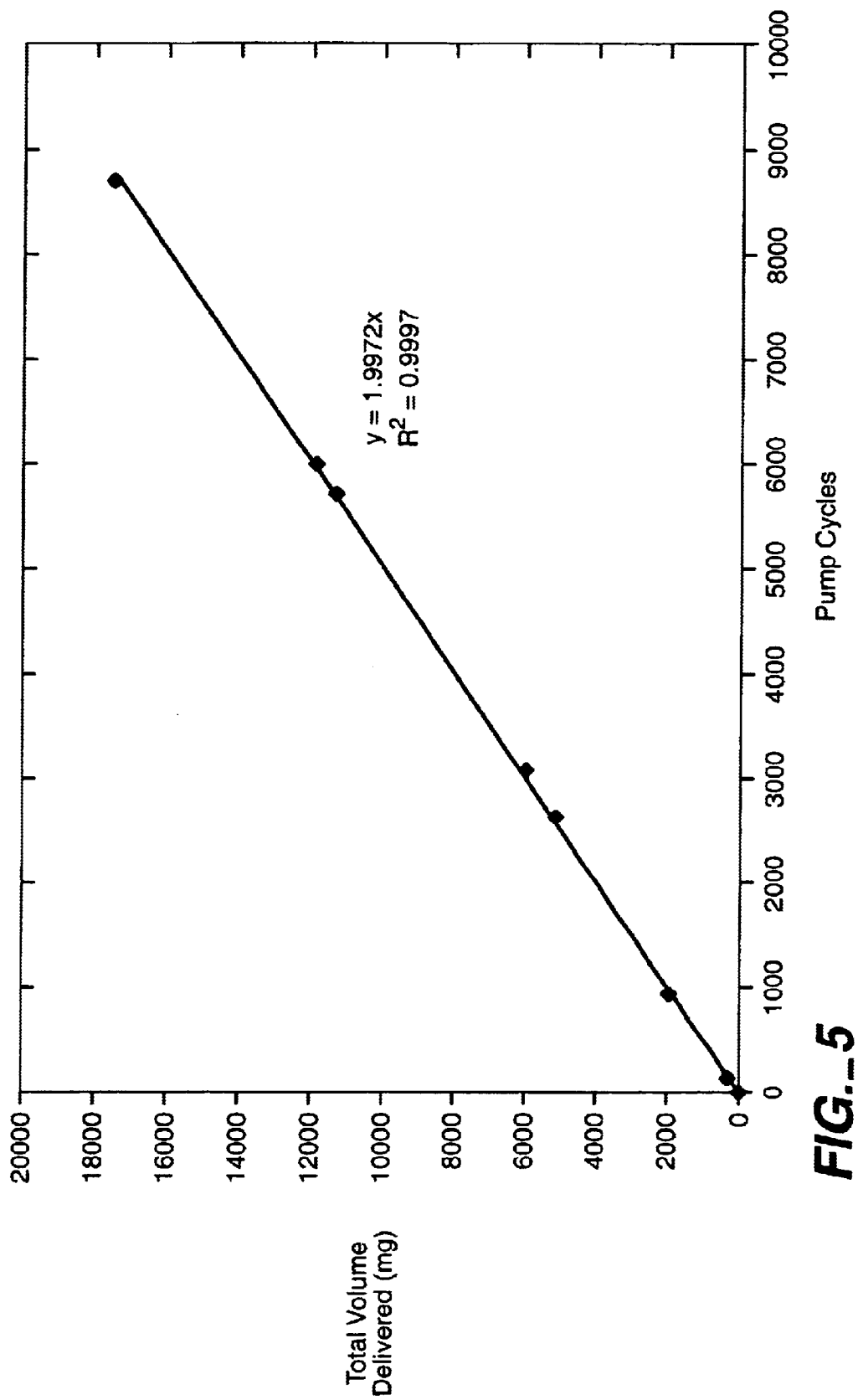
FIG._5

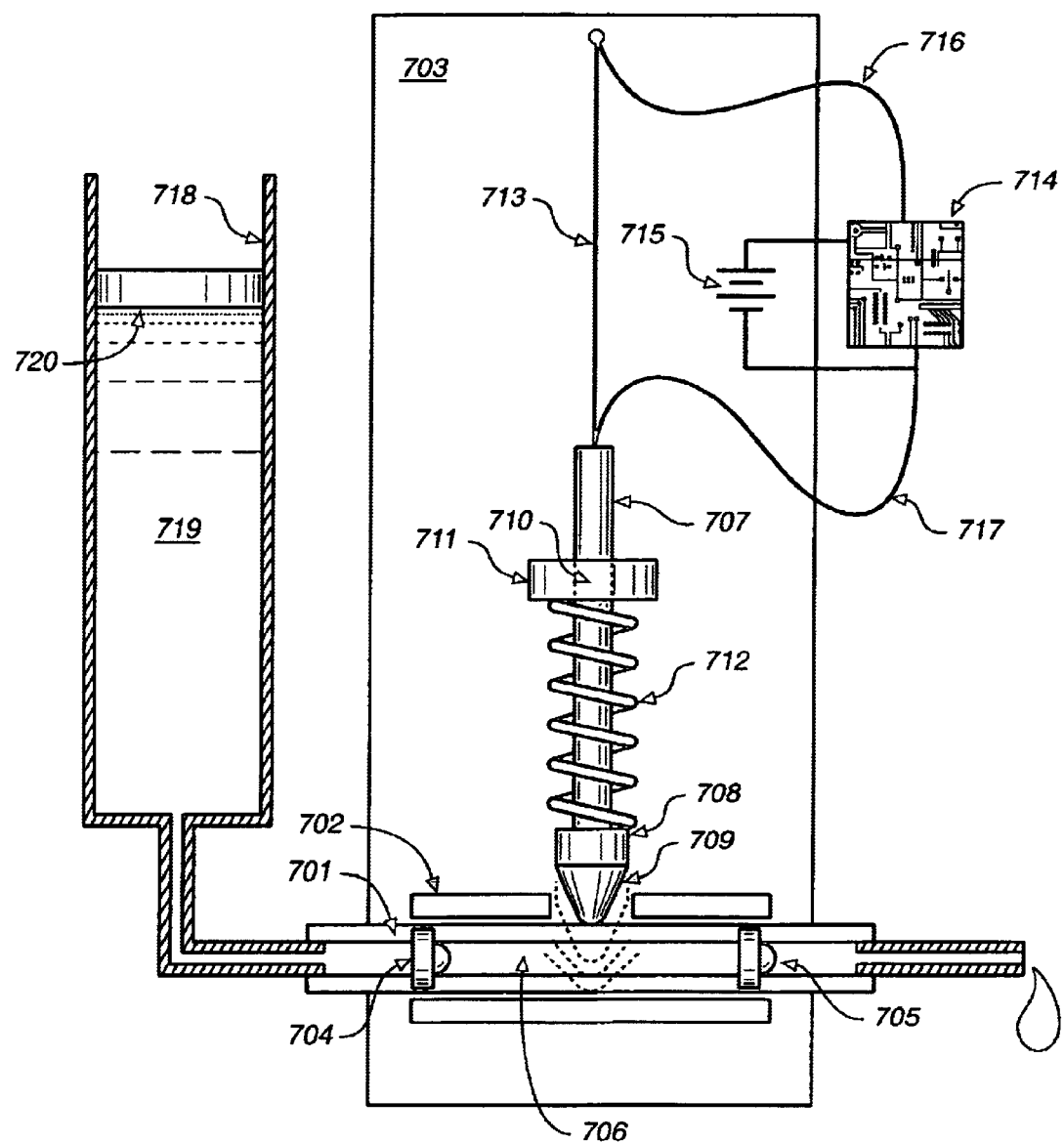
FIG._7

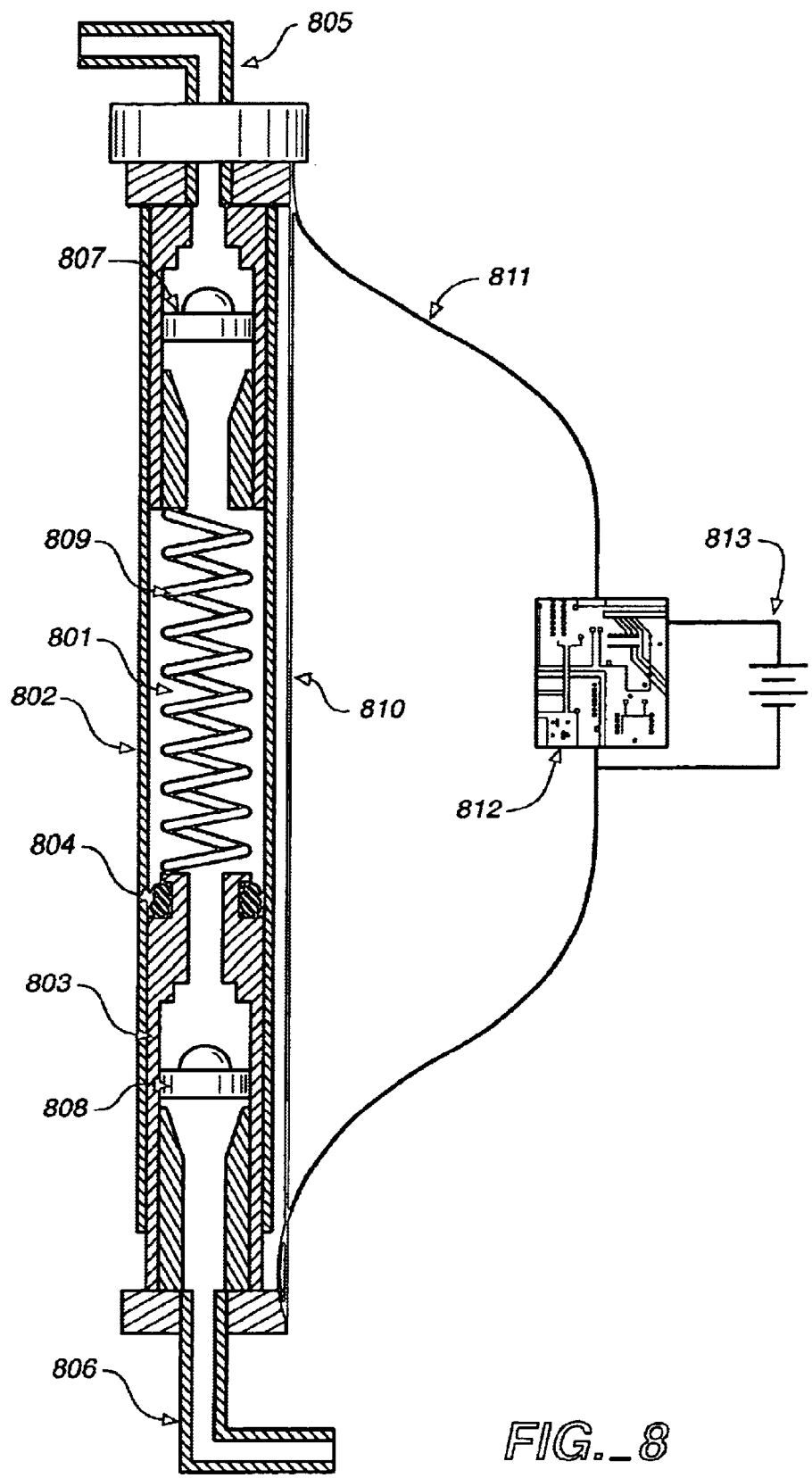
FIG._8

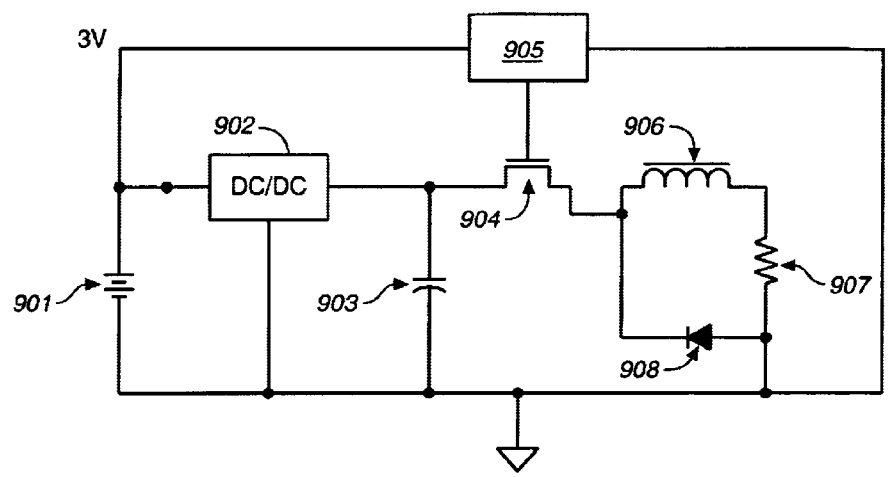
FIG._9

DEVICE AND METHOD EMPLOYING SHAPE MEMORY ALLOY

CROSS-REFERENCE TO RELATED APPLICATIONS

This non-provisional application is related to and claims priority based on U.S. Provisional Application No. 60/417,464, entitled "Disposable Pump For Drug Delivery System," filed on Oct. 9, 2002 and U.S. Provisional Application No. 60/424,613, entitled "Disposable Pump And Actuation Circuit For Drug Delivery System," filed on Nov. 6, 2002, each of which is incorporated herein in its entirety by this reference. This non-provisional application is also related to U.S. Provisional Application No. 60/424,414, entitled "Automatic Biological Analyte Testing Meter With Intergrated Lancing Device And Methods Of Use," filed Nov. 6, 2002, and U.S. Pat. No. 6,560,471, entitled "Analyte Monitoring Device and Methods of Use," issued May 6, 2003, each of which is incorporated herein in its entirety by this reference.

FIELD OF INVENTION

This invention generally relates to fluid delivery devices, systems, and methods. This invention further relates to small volume, disposable medical devices for the precision delivery of medicines or drugs such as insulin, and associated systems and methods.

BACKGROUND OF THE INVENTION

Insulin pumps are widely available and are used by diabetic people to automatically deliver insulin over extended periods of time. All currently available insulin pumps employ a common pumping technology, the syringe pump. In a syringe pump, the plunger of the syringe is advanced by a lead screw that is turned by a precision stepper motor. As the plunger advances, fluid is forced out of the syringe, through a catheter to the patient. The choice of the syringe pump as a pumping technology for insulin pumps is motivated by its ability to precisely deliver the relatively small volume of insulin required by a typical diabetic (about 0.1 to about 1.0 $cm^3$ per day) in a nearly continuous manner. The delivery rate of a syringe pump can also be readily adjusted through a large range to accommodate changing insulin requirements of an individual (e.g., basal rates and bolus doses) by adjusting the stepping rate of the motor. While the syringe pump is unparalleled in its ability to precisely deliver a liquid over a wide range of flow rates and in a nearly continuous manner, such performance comes at a cost. Currently available insulin pumps are complicated and expensive pieces of equipment costing thousands of dollars. This high cost is due primarily to the complexity of the stepper motor and lead screw mechanism. These components also contribute significantly to the overall size and weight of the insulin pump. Additionally, because of their cost, currently available insulin pumps have an intended period of use of up to two years, which necessitates routine maintenance of the device such as recharging the power supply and refilling with insulin.

U.S. Pat. No. 6,375,638 of Clyde Nason and William H. Stutz, Jr., entitled "Incremental Motion Pump Mechanisms Powered by Shape Memory Alloy Wire or the Like," issued Apr. 23, 2002, and naming Medtronic MiniMed, Inc. as the assignee, which patent is incorporated herein in its entirety by this reference, describes various ratchet type mechanisms for incrementally advancing the plunger of a syringe pump. The ratchet mechanisms are actuated by a shape memory alloy wire. The embodiments taught by Nason et. al involve a large number of moving parts, and are mechanically complex, which increases size, weight and cost, and can reduce reliability.

SUMMARY OF THE DISCLOSURE

A fluid delivery system constructed according to the present invention can be utilized in a variety of applications. As described in detail below, it can be used to deliver medication to a person or animal. The invention can be applied in other medical fields, such as for implantable micro-pump applications, or in non-medical fields such as for small, low-power, precision lubricating pumps for precision self-lubricating machinery.

In its preferred embodiment, the present invention provides a mechanical insulin delivery device for diabetics that obviates the above-mentioned limitations of the syringe pump namely size, weight, cost and complexity. By overcoming these limitations, a precise and reliable insulin delivery system can be produced with sufficiently low cost to be marketed as a disposable product and of sufficiently small size and weight to be easily portable by the user. For example, it is envisioned that such a device can be worn discretely on the skin as an adhesive patch and contain a three-day supply of insulin after the use of which the device is disposed of and replaced.

The present invention relates to a miniature precision reciprocating displacement pump head driven by a shape memory alloy actuator. Shape memory alloys belong to a class of materials that undergo a temperature induced phase transition with an associated significant dimensional change. During this dimensional change, shape memory alloys can exert a significant force and can thus serve as effective actuators. The shape memory alloy actuator provides an energy efficiency about one thousand times greater than that of a conventional electromechanical actuator, such as a solenoid, and a force to mass ratio about ten thousand times greater. Additionally, the cost of shape memory alloy materials compares favorably to the cost of electromechanical devices with similar capabilities.

The device of the present invention is intended to be operated in a periodic dosing manner, i.e., liquid is delivered in periodic discrete doses of a small fixed volume rather than in a continuous flow manner. The overall liquid delivery rate for the device is controlled and adjusted by controlling and adjusting the dosing period. Thus the device employs a precision timing mechanism in conjunction with a relatively simple mechanical system, as opposed to a complex mechanical system, such as that embodied by the syringe pump. A precision timing device is an inherently small, simple and inexpensive device. It is an underlying assumption of the invention (and a reasonable conclusion of process control theory) that in the treatment of diabetes, there is no clinical difference between administering insulin in periodic discrete small doses and administering insulin in a continuous flow, as long as the administration period of the discrete dose is small compared to the interval of time between which the blood glucose level is measured. For the present invention, a small dose size is regarded as on the order of 0.10 units of insulin (1 microliter) assuming a standard pharmaceutical insulin preparation of 100 units of insulin per ml (U 100). A typical insulin dependent diabetic person uses between 10 and 100 units of insulin per day, with the average diabetic person using 40 units of insulin. Thus the present invention would deliver the daily insulin requirements of the average diabetic person in 400 individual discrete doses of 1 µl each with a dosing period that can be programmed by the user. A pump constructed according to the present invention can have a predetermined discrete dosage volume that is larger or smaller than 1 µl, but preferably falls within the range of 0.5 to 5 µl, and more preferably falls within the range of 1 to 3 µl. The smaller the discrete dose is of a particular pump design, the more energy required by the device to deliver a given amount of fluid, since each pump cycle consumes roughly the same amount of energy regardless of discrete dosage size. On the other hand, the larger the discrete dosage is, the less precisely the pump can mimic the human body in providing a smooth delivery rate. A device constructed according to the present invention is also suitable for delivery of other drugs that might be administered in a manner similar to insulin.

It is further intended that the present invention could be used as a disposable component of a larger diabetes management system comprised of additional disposable and non-disposable components. For example, the present invention could be coupled with a continuous blood glucose monitoring device and remote unit, such as a system described in U.S. Pat. No. 6,560,471, entitled "Analyte Monitoring Device and Methods of Use," issued May 6, 2003. In such an arrangement, the hand-held remote unit that controls the continuous blood glucose monitoring device could wirelessly communicate with and control both the blood glucose monitoring unit and the fluid delivery device of the present invention. The monitor and pump could be physically separate units, or could share one or more disposable and/or non-disposable components. For example, a disposable pump constructed according to the present invention and charged with a 3-day supply of insulin, a small battery and a disposable glucose sensor could be integrated into a single housing and releasably coupled with non-disposable components such as control electronics, a transmitter/receiver and a user interface to comprise a small insulin delivery device that could be worn on the skin as an adhesive patch. Alternatively, the battery (or batteries) and/or sensor could be replaced separately from the disposable pump. Such arrangements would have the advantage of lowering the fixed and recurring costs associated with use of the invention.

BRIEF DESCRIPTION OF THE DRAWINGS

A detailed description of various embodiments of the invention is provided herein with reference to the accompanying drawings, which are briefly described below.

FIG. 1A shows a schematic representation of a most general embodiment of the invention.

FIG. 1B shows a schematic representation of an alternative general embodiment of the invention.

FIG. 2A shows a schematic representation of a preferred embodiment of the invention.

FIGS. 2B and 2C show enlarged details of a preferred embodiment of the invention.

FIG. 3 shows a schematic representation of a preferred embodiment of a check valve to be used in the invention.

FIG. 4 shows a schematic representation of a preferred embodiment of a pulse generation circuit to be used with the invention.

FIG. 5 shows data from the experimental characterization of the reproducibility of a functional model of the invention.

FIG. 7 shows a schematic representation of a first alternative embodiment of the invention.

FIG. 8 shows a schematic representation of a second alternative embodiment of the invention.

FIG. 9 shows a schematic representation of a first alternative embodiment of a pulse generation circuit to be used with the invention.

DETAILED DESCRIPTION OF A MOST GENERAL EMBODIMENT OF THE INVENTION

Figure 6:
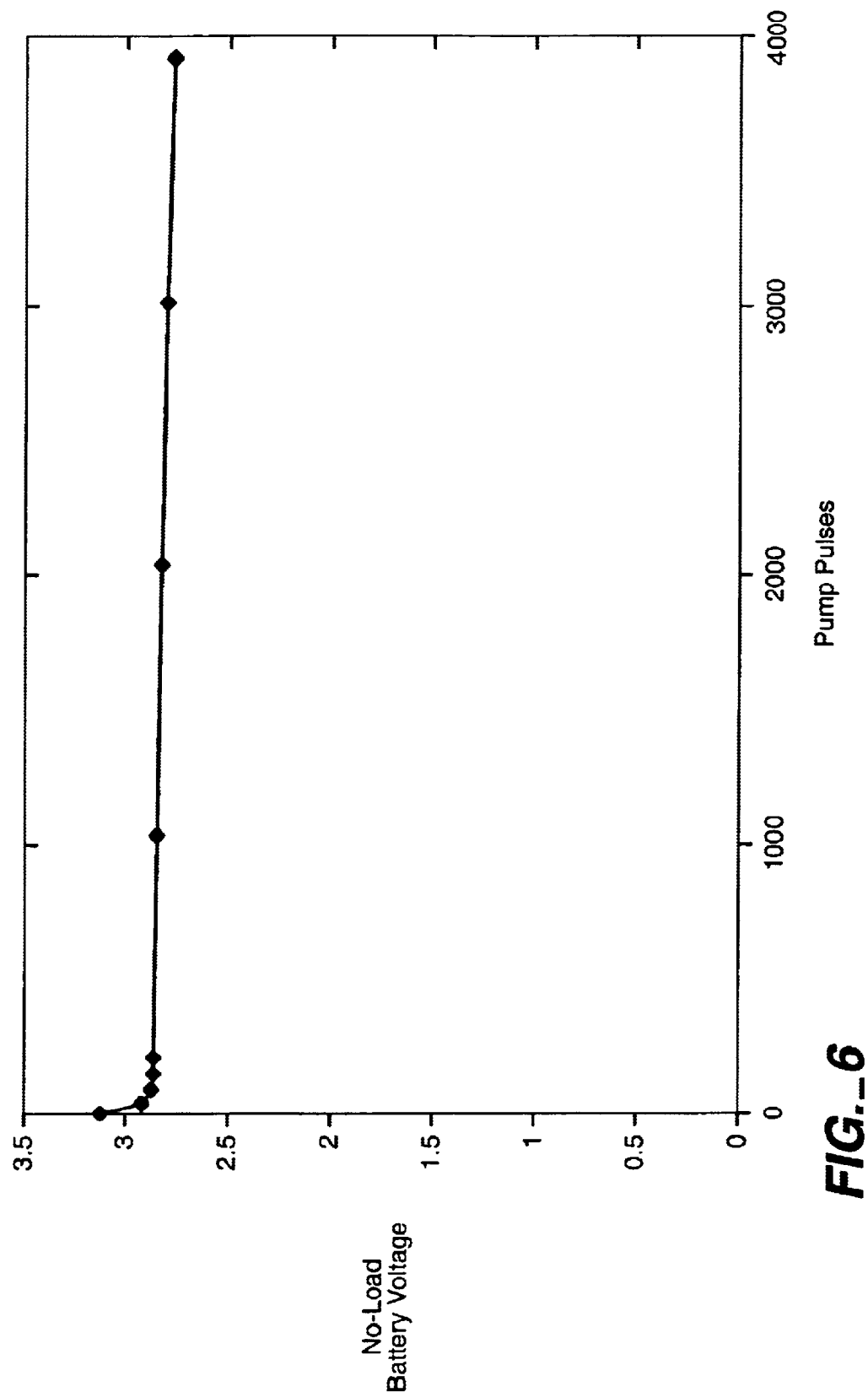
FIG. 6 shows data from the experimental characterization of the energy utilization of a functional model of the invention.

A device of the present invention includes a miniature precision reciprocating displacement pump driven by a shape memory alloy wire linear actuator and controlled by a programmable pulse generating circuit. For purposes of description, the device is divided into three subcomponents, a precision miniature reciprocating displacement pump head, a shape memory alloy linear actuator, and a programmable pulse generating circuit. Each subcomponent is comprised of multiple elements. A schematic representation of a most general embodiment of the invention is shown in FIG. 1A and is described below.

The miniature precision pump head is comprised of the following elements: a rigid substrate 101 to which other components may be attached so as to fix their orientation and position relative to one another, a fluid reservoir 102 for storing the fluid to be pumped 103 and a small cavity, henceforth referred to as the displacement cavity 104, whose volume can be varied between precisely defined limits. The limit corresponding to a state of maximum volume for the displacement cavity 104 is defined as the first limit 105 and the limit corresponding to a state of minimum volume for the displacement cavity 104 is defined as the second limit 106. An inlet conduit 107 connects the displacement cavity 104 to the fluid reservoir 102 and thus permits fluid flow between the two. An inlet check valve 108 is situated within the inlet conduit 107 such that fluid flow is restricted to flowing from the fluid reservoir 102 to the displacement cavity 104. An outlet conduit 109 connects the displacement cavity 104 to some point 111 to which it is desired to deliver the fluid. An outlet check valve 110 is situated within the outlet conduit 109 such that fluid flow is restricted to flowing from the displacement cavity 104 to the point 111 to which it is desired to deliver the fluid.

The shape memory alloy actuator is comprised of a shape memory allow material, such as a nickel-titanium alloy material, sometimes referred to as "nitinol." The shape memory alloy material is sensitive to temperature or heat. For example, the material temporarily shrinks at a certain temperature, or shrinkage temperature, such as about 70° C. above ambient temperature for nitinol, and expands at a relatively lower temperature to return to its original condition. In response to being heated to the above-described shrinkage temperature, the shape memory alloy undergoes a dimensional change, such as a change in its length. In this way, a wire composed of a material such as nitinol, can undergo a change in length and a return toward its original length one or more times via temperature treatment or repeated temperature cycling. It is contemplated that a material that expands by going through a phase transition at a certain temperature and shrinks at a different temperature to return toward its original condition could be used.

In the process of undergoing a dimensional change, as described above, the shape alloy material goes through a reversible phase transition or transformation, or a reversible structural phase transition, upon a change in temperature.

Generally, such a transition represents a change in the material from one solid phase of the material to another, for example, by virtue of a change in the crystal structure of the material or by virtue of a reordering of the material at a molecular level. In the case of nitinol, for example, the superelastic alloy has a low temperature phase, or martensitic phase, and a high temperature phase, or austenitic phase. These phases can also be referred to in terms of a stiff phase and a soft and malleable phase, or responsive phase. The particular phase transition associated with a particular alloy material may vary.

The shape memory alloy actuator is also comprised of the following elements. A movable member is referred to as a plunger 112 and is fixed by a rigid restraint 113 such that it is constrained to a periodic motion of precisely fixed limits. The plunger 112 is situated in relation to and/or attached to the displacement cavity 104 such that movement of the plunger 112 within the limits of its constrained motion will cause the volume of the displacement cavity 104 to be varied between its limits 105, 106. A biasing spring 115 is situated relative to the rigid restraint 113 and the plunger 112 such that at equilibrium, the biasing spring 115 exerts a force on the plunger 112 whose direction is that which would induce the displacement cavity 104 toward a state of minimum volume, i.e., toward its second limit 106. A length of shape memory alloy wire 114 is connected at one end to the plunger 112 and at another end to the rigid substrate 101. The shape memory alloy wire 114 is situated such that its dimensional change will give rise to motion of the plunger 112. The shape memory alloy wire 114 and the biasing spring 115 are both of sufficient dimension such that when the shape memory alloy wire 114 is heated so as to induce phase transition and associated dimensional change, the wire will move the plunger 112 against the force of the biasing spring 115 "in one generally uninterrupted motion" to its second limit 105 so as to create a state of maximum volume within the displacement cavity 104, whereas when the shape memory alloy is allowed to cool to ambient temperature, the force imparted by the biasing spring 115 will stretch the shape memory alloy wire 114 until the point where the displacement cavity 104 is in a state of minimum volume.

The programmable pulse generating circuit is comprised of a source of electric power 116, an electrical connection 117 from the source of electric power 116 to each end of the shape memory alloy wire 114 and a programmable pulse generating circuit 118 situated along the electrical connection 117 such that pulses of electricity from the electric power source 116 may be applied to the shape memory alloy wire 114 automatically in a preset regular periodic manner.

Operation of the device proceeds in a cyclic manner. For purposes of description the beginning of the cycle is defined as the following state. All void space within the fluid reservoir 102, inlet 107 and outlet 109 conduit, inlet 108 and outlet 110 check valves and displacement cavity 104 are completely filled with the fluid 103 to be pumped. The shape memory alloy wire 114 is at ambient temperature and thus in a state of maximum length. Correspondingly, the position of the plunger 112 is such that the volume of the displacement chamber 104 is at its minimum value. The biasing spring 115 is in a compressed state such that it exerts a force on the plunger 112 consistent with a state of minimum volume of the displacement cavity 104. Operation of the device involves first a heating of the shape memory alloy wire 114 to a temperature and for a period of time sufficient to induce phase transition and an associated dimensional change. Heating of the shape memory alloy wire 114 is accomplished by passing an electric current though it. The duration of the electric heating period is preset and is controlled by the timing and switching circuit 118. The dimensional change of the shape memory alloy wire 114 will result in the movement of the plunger 112 against the opposing force of biasing spring 115 so as to vary the volume of the displacement chamber 104 toward its first limit 105 and a state of maximum volume. As the volume of the displacement cavity 104 is increased, fluid 103 is drawn into the displacement cavity 104 from the fluid reservoir 102 through the inlet conduit 107 and inlet check valve 108. Fluid 103 is not drawn into the displacement cavity 104 through the outlet conduit 109 due to the one-way flow restriction of the outlet check valve 110. After the preset duration, the current is then switched off by the timing and switching circuit 118 allowing the shape memory alloy wire 114 to cool below its phase transition temperature. Cooling proceeds via natural convection to the ambient environment. When the shape memory alloy wire 114 cools below its phase transition temperature, the force exerted by the biasing spring 115 stretches the shape memory alloy wire 114 to its original maximum length. This allows the movement of the plunger 112 so as to vary the volume of the displacement cavity 104 toward its second limit 106 and a state of minimum volume. As the volume of the displacement cavity 104 is decreased, fluid 103 is pushed out of the displacement cavity 104 through the outlet conduit 109 and outlet check valve 110. Fluid 103 is not pushed out of the displacement cavity 104 through the inlet conduit 107 due to the one-way flow restriction of the inlet check valve 108. Thus one complete heating and cooling cycle of the shape memory alloy wire 114 results in the delivery of a volume of fluid 103 from the fluid reservoir 102 to the end of the outlet conduit 111. The volume of fluid delivered with each cycle is precisely equal to the difference between the maximum and minimum volumes of the displacement cavity 104 as determined by the precisely defined limits 105, 106. The overall rate of fluid delivery is controlled by varying the period of time between actuations of the shape memory alloy actuator 104.

An Alternative General Embodiment of the Invention

A schematic representation of an alternative general embodiment of the invention is shown in FIG. 1B. The alternative general embodiment includes all of the same components and elements as the general embodiment shown in FIG. 1A with the following exceptions. In this embodiment of the invention, heating of the shape memory alloy material 114 so as to cause a phase transition associated shortening of its length results in a minimum volume condition for the displacement cavity 104. This may be achieved, for example, through the use of a pivoting linkage assembly 119 connecting the biasing spring 115 to the plunger 112.

Detailed Description of a Preferred Embodiment of the Invention

As stated previously, it is an intention of the present invention that it be sufficiently small and sufficiently inexpensive to be practically used as both a portable device and as a disposable device. For example, a device that can be comfortably worn on the skin as an adhesive patch and can be disposed of and replaced after 3 days of use. A preferred embodiment of the invention includes specific embodiments of the various elements and components of the general embodiment that are consistent with this intention.

A preferred embodiment of the invention is diagrammed schematically in FIGS. 2A, 2B and 2C and is comprised of all of the same elements and components of the general embodiment of the invention shown in FIGS. 1A and 1B with the following exceptions. In a preferred embodiment of the invention the displacement cavity is comprised of an elastomeric diaphragm pump head 201. An enlarged view of the details of the diaphragm pump head 201 is shown by FIG. 2B with pump head 201 in a state of minimum volume and by FIG. 2C with pump head 201 in a state of maximum volume. The diaphragm pump head is comprised of an elastomeric diaphragm 202 set adjacent to a rigid substrate 203 and sealed about a perimeter of the elastomeric diaphragm 202. The displacement cavity 204 is then comprised of the volume in between the adjacent surfaces of the rigid substrate 203 and the elastomeric diaphragm 202 within the sealed perimeter.

Separate inlet 205 and outlet 206 conduits within the rigid substrate 203 access the displacement volume of the elastomeric diaphragm pump head 201 with the inlet conduit 205 connecting the displacement cavity 204 with a fluid reservoir 207 and the outlet conduit 206 connecting the displacement cavity 204 to the point to which it is desired to deliver fluid 208. An inlet check valve 209 and an outlet check valve 210 are situated within the inlet conduit 205 and outlet conduit 206 respectively, oriented such that the net direction of flow is from the fluid reservoir 207 to the point to which it is desired to deliver fluid 208.

The plunger 211 is comprised of a cylindrical length of rigid dielectric material. The plunger 211 is situated within a cylindrical bore 212 of a rigid restraint 213 such that the axis of the plunger 211 is oriented normal to surface of the elastomeric diaphragm 202. The flat head of the plunger 211 is functionally attached to the non-wetted surface of elastomeric diaphragm 202 opposite the displacement cavity 204 such that movement of the plunger 211 along a line of motion coincident with its axis will cause the concomitant variation in the volume of the displacement cavity 204. The biasing spring 214 is situated within the cylindrical bore 212 of the rigid restraint 213, coaxial with the plunger 211. The relative positions and dimensions of the plunger 211, the rigid restraint 213 and the biasing spring 214 are such that at equilibrium the biasing spring 214 exerts a force on the plunger 211 along a line coincident with its axis such that the displacement cavity 204 is in a state of minimum volume (FIG. 2A).

A straight length of shape memory alloy wire 215 is situated in a position coincident with the axis of the plunger 211. One end of the shape memory alloy wire 215 is fixed to the rigid restraint 203 and electrically connected by connection 216 to the programmable pulse generating circuit 217 and the electric power source 218. The other end of the shape memory alloy wire 215 along with an electrical connection 219 to that end is connected to the end of the plunger 211. The shape memory alloy wire 215 and the biasing spring 214 are both of sufficient dimension such that when the shape memory alloy wire 215 is heated so as to induce phase transition and associated dimensional change, it will pull the plunger 211 against the force of the biasing spring 214 so as to create a state of maximum volume within the displacement cavity 204, whereas when the shape memory alloy is allowed to cool to ambient temperature, the force imparted by biasing spring 214 will stretch the shape memory alloy wire 215 until the point where the displacement cavity 204 is in a state of minimum volume.

A preferred embodiment of an inlet and outlet check valve is shown in cross-section in FIG. 3 and is comprised of a molded one-piece elastomeric valve which can be press-fit into the inlet or outlet conduit. An important feature for a check valve appropriate for use in the present invention is that it possesses a low cracking pressure and provides a tight seal in the absence of any back pressure. A preferred embodiment of such a check valve is comprised of a thin-walled elastomeric dome 301 situated on top of a thick elastomeric flange 302. The top of the dome has a small slit 303 cut through it that is normally closed. A fluid pressure gradient directed toward the concave side 304 of the dome will induce an expansion of the dome 301 forcing the slit 303 open so as to allow fluid to flow through the valve in this direction. A fluid pressure gradient directed toward the convex side 305 of the dome will induce a contraction of the dome 301 forcing the slit 303 shut so as to prohibit fluid to flow through the valve in this direction.

A preferred embodiment of a pulse generating circuit is shown in FIG. 4 and is comprised of a 200 milliamp-hour, lithium-manganese oxide primary battery 401, a high-capacitance, low-equivalent series resistance (ESR) electrochemical capacitor 402, a programmable digital timing circuit 403, and a low-resistance field effect transistor switch 404. The shape memory alloy wire is indicated in FIG. 4 symbolically as a resistor 405. The battery 401 and electrochemical capacitor 402 are electrically connected to each other in parallel and are connected to the shape memory alloy wire 405 through the transistor switch 404. The programmable timing circuit 403, also powered by the battery 401, sends a gating signal to the transistor switch 404, as programmed by the user in accordance with the user's pumping requirements. During the period of time for which the transistor switch 404 is open, the battery 401 will keep the electrochemical capacitor 402 at a state of full charge. During the period of time for which the transistor switch 404 is closed, power will be delivered to the shape memory alloy wire 405, primarily from the electrochemical capacitor 402 rather than from the battery 401, owing to the substantially lower ESR associated with the electrochemical capacitor 402. As such, the battery 401 is substantially isolated from the high current draw associated with the low resistance of the shape memory alloy wire 405 and the useful life of the battery 401 is significantly extended.

A preferred embodiment of a fluid reservoir 207 appropriate for use with the present invention is one for which the volume of the fluid reservoir diminishes concomitantly as fluid is withdrawn such that it is not necessary to replace the volume of the withdrawn fluid with air or any other substance. A preferred embodiment of a fluid reservoir 207 might comprise a cylindrical bore 220 fitted with a movable piston 221 for example, a syringe, or a balloon constructed of a resilient material.

Operation of the preferred embodiment of the invention proceeds in a manner analogous to that described for the most general embodiment. In addition to its simplicity, the preferred embodiment has the advantage of physically blocking any fluid flow from the fluid reservoir to the point to which it is desired to deliver the fluid when there is no power being supplied to the system. This provides additional protection against an overdose caused by fluid expanding or being siphoned through the check valves when the system is inactive.

Detailed Description of a Functional Model of the Invention

A functional model of a preferred embodiment of the invention has been constructed and its performance has been characterized. The functional model is similar in appearance to the preferred embodiment of the invention shown in FIGS. 2, 3 and 4 and is described in more detail below. The fixed rigid components of the pump including the rigid restraint and the rigid substrate of the diaphragm pump head are each machined from a monolithic block of acetal. Inlet and outlet conduits are additionally machined out of the same block. Check valves are commercially available one-piece elastomeric valves (for example, Check Valve, Part # VA4914, available from Vernay Laboratories Inc. of Yellow Springs, Ohio). A length of shape memory alloy actuator is 40 mm long and 125 $\mu$m in diameter (for example, Shape Memory Alloy Wire, Flexinol 125 LT, available from Mondo-tronics, Inc. of San Rafael, Calif.). Electrical connections to the ends of the shape memory alloy actuator are made with 30 AWG copper wire. The copper wire is twisted to the shape memory alloy wire to effect a good electrical connection. A plunger is machined out of acetal and has an overall length of 10.0 mm and a shaft diameter of 3.2 mm. An elastomer diaphragm is comprised of 0.025 mm thick silicon rubber film (for example, Silicon Rubber Film, Cat. # 86435K31, available from McMaster Carr, of Los Angeles, Calif.). The flat head of the plunger is secured to the elastomer diaphragm with epoxy (for example, Epoxy, Stock #14250, available from ITW Devcon, of Danvers, Mass.). The ends of the shape memory alloy wire-copper conductor assembly are connected to the plunger and to the rigid restraint with epoxy. A stainless steel biasing spring has an overall length of 12.7 mm, an outside diameter of 3.0 mm, a wire diameter of 0.35 mm and a spring constant of 0.9 N/mm (for example, Biasing Spring, Cat. # C0120-014-0500, available from Associated Spring, of Dallas, Tex.).

A pulse generating circuit is comprised of an adjustable analog timing circuit based on a 556 dual timing integrated circuit (for example, 556 Dual Timing Circuit, Part # TS3V556, available from ST Microelectronics, of San Jose, Calif.). Power is supplied by a 3 V lithium-manganese dioxide primary cell (for example, Li/MgO$_2$ Battery, Part # DL2032, available from Duracell, of Bethel, Conn.). Power load leveling is facilitated by the use of an electrochemical supercapacitor (for example, Electrochemical Supercapacitor, Part # B0810, available from PowerStor Inc., of Dublin, Calif.) in parallel with the battery. High-power switching is achieved with a field effect transistor (for example, Field Effect Transistor Switch, Part # IRLZ24N, available from International Rectifier, of El Segundo, Calif.).

The functional model was characterized with respect to reproducibility, insulin stability and energy consumption. The model was operated by heating the shape memory alloy wire with a short pulse of current and then allowing the shape memory alloy wire to cool. Each heating pulse and subsequent cooling period comprised a single actuation cycle.

A device that is used to automatically deliver a drug to an individual over an extended period of time should do so with extreme precision. This is particularly critical when the drug being delivered is one that might have dangerous health consequences associated with an inappropriate dose. Insulin is one such drug. An excessive dose of insulin can result in dangerously low blood glucose level, which in turn can lead to coma and death. Thus any device to be used for automatically delivering insulin to a diabetic person must be able to demonstrate a very high level of precision. To characterize the precision with which the invention can deliver insulin, the functional model was repeatedly cycled at a constant period of actuation and the total quantity of liquid delivered was measured as a function of the number of actuation cycles. FIG. 5 shows typical results. The data in FIG. 5 were obtained with an actuation period of 28 seconds and a pulse duration of 0.15 seconds. In FIG. 5 markers show actual data points and the line represents a least squares fit of the data points. Data were collected over 8500 cycles at which point the measurement was stopped. The fit to the data has a slope of 1.997 mg/cycle and a linear correlation coefficient of 0.999 indicating that the functional model delivered extremely consistent volumes of liquid with each actuation over the course of the measurement.

Another important requirement for any medical device that handles insulin is that the device does not damage the insulin. Insulin is a large and delicate biomolecule that can readily be damaged by the mechanical action (e.g., shear stress) of a pumping device. Three common modes of insulin destruction which result in a loss of bioactivity are aggregation, where individual insulin molecules bond together to form various polymer structures, degradation, where individual insulin molecules are broken apart, and denaturing, where individual molecules remain intact but lose their characteristic conformation. All three modes of insulin destruction are exacerbated by elevated temperatures. Thus, in the development of a practical insulin pumping device, preferably, it should be demonstrated that the device does not damage insulin. To characterize the insulin stability associated with the invention, a quantity of insulin (Insulin, Humalog U100, available from Eli Lilly, of Indianapolis, Ind.) was set up to recycle continuously through the functional model over the course of several days at 37° C. Samples of the insulin were collected each day for evaluation. This resulted in a series of pumped insulin samples with an increasing amount of pump stress. The insulin samples were then analyzed by reverse-phase high performance liquid chromatography. The chromatography indicated a 2% loss of insulin concentration after a single pass through the pump and a further loss of another 5% of the insulin concentration after 3 days of recycling.

It is desirable for a small and inexpensive insulin delivery device to be able to execute its maximum intended term of use with the energy from a single small inexpensive primary battery. Based on a 0.1 unit dose size and a maximum insulin consumption of 100 units per day for 3 days, a maximum term of use for the inventive device might be considered to be 3000 cycles. To characterize the energy consumption of the invention, the functional model was operated continuously for several days at an actuation period of 85 seconds while the voltage of a 200 milliamp-hour, 2032 lithium/manganese dioxide battery was monitored. FIG. 6 shows typical results. A typical voltage vs. capacity curve for the lithium/manganese dioxide battery is characterized by an initial drop in voltage from about 3.2 V to a plateau voltage of about 2.8 V. The voltage of the battery remains at this plateau level for the duration of its useful life. The battery voltage will then drop precipitously to a value below 2 V when its capacity expires. The data in FIG. 6 indicate that the battery is still at its plateau voltage after 4000 pump cycles and thus the 200 milliamp-hour, lithium/manganese dioxide battery is more than adequate to power the device of the present invention for its intended term of use.

Alternative Embodiments of the Invention

A first alternative embodiment of the invention is diagrammed schematically in FIG. 7 and is comprised of all of the same subcomponents and elements of the most general embodiment of the invention shown in FIG. 1 with the following exceptions. In a first alternative embodiment of the invention, the displacement cavity, as well as the inlet and outlet conduit, are all comprised of a single length of small-diameter flexible and resilient tubing 701. The tubing 701 is situated within a restraining fixture 702 secured to a rigid base 703 so as to fix the position and orientation of the tubing 701 relative to the other elements of the device. Inlet 704 and outlet 705 check valves are located within the bore of the tubing 701 such that they have a common orientation for flow direction and such that a length of empty tubing 701 exists in between the two check valves 704, 705. The volume within the inner diameter of the tubing 701 and in between the two check valves 704, 705 comprises a displacement cavity 706. The volume of the displacement cavity 706 is varied by compressing the resilient tubing 701 with a plunger 707 (described below) at a position midway between the two check valves 704, 705. The volume within the inner diameter of the tubing 701 and in between the two check valves 704, 705 when the tubing 701 is uncompressed defines the maximum volume of displacement cavity 706. The volume within the inner diameter of the tubing 701 and in between the two check valves 704, 705 when the tubing 701 is fully compressed defines the minimum volume of the displacement cavity 706.

The plunger 707 is comprised of a cylindrical length of rigid dielectric material and includes a flange 708 and a tapered end 709. The plunger 707 is situated within a cylindrical bore 710 of a rigid restraint 711 such that the axis of the plunger 707 is oriented normal to the axis of the resilient tubing 701 and such that the tapered head 709 of the plunger 707 may be alternately pressed against the resilient tubing 701 and removed from contact with the resilient tubing 701 with movement of the plunger 707 along a line of motion coincident with the its axis. A biasing spring 712 is fitted around the shaft of the plunger 707 in between the rigid restraint 711 and the plunger flange 708. The relative positions and dimensions of the plunger 707, the rigid restraint 711 and the biasing spring 712 are such that at equilibrium the biasing spring 712 exerts a force on the plunger 707 along a line coincident with its axis that is sufficient to fully collapse the resilient tubing 701 and thus create a state of minimum volume of the displacement cavity 706.

A straight length of shape memory alloy wire 713 is situated in a position coincident with the axis of the plunger 707. One end of the shape memory alloy wire 713 is attached to the rigid base 703 and electrically connected by connection 716 to the pulse generating circuit 714 and the electric power source 715. The other end of the shape memory alloy wire 713 along with an electrical connection 717 to that end is attached to the shaft of the plunger 707. The shape memory alloy wire 713 is of sufficient length and strength that when heated so as to induce phase transition and associated dimensional change it will pull the plunger 707 away from contact with the resilient tubing 701 against the opposing force of the biasing spring 713. Much as described in relation to FIG. 2A, a preferred embodiment of a fluid reservoir 719 appropriate for use with the present invention is one for which the volume of the fluid reservoir diminishes concomitantly as fluid is withdrawn such that it is not necessary to replace the volume of the withdrawn fluid with air or any other substance. A preferred embodiment of a fluid reservoir 719 might comprise a cylindrical bore 718 fitted with a movable piston 720, for example, a syringe, or a balloon constructed of a resilient material.

A second alternative embodiment of the invention is diagrammed schematically in FIG. 8 and is comprised of all of the same subcomponents and elements of the most general embodiment of the invention shown in FIG. 1 with the following exceptions. A displacement cavity 801 is comprised of a cylindrical shell 802 and tube 803 arrangement where the tube 803 is coaxial with the shell 802 and can move freely within the shell 802 along a line coincident with that axis. The volume of the displacement cavity 801 is varied by moving the tube 803 relative to the shell 802. Movement of the tube 803 into the shell 802 reduces the volume of the displacement cavity 801 whereas movement of the tube out of the shell increases the volume of the displacement cavity 801. A dynamic seal 804, for example and elastomer o-ring, seals the displacement cavity 801 while not interfering adversely with the relative motion of the shell 802 and tube 803. Outlet 805 and inlet 806 conduits access the displacement cavity 801 through the ends of the shell 802 and tube 803 respectively. Outlet 807 and inlet 808 check valves are situated within the shell 802 and tube 803 respectively. A biasing spring 809 is situated within the displacement cavity 801 so as to resist the motion of the displacement cavity 801 toward a state of reduced volume. A shape memory alloy wire 810 is attached between the shell 802 and the tube 803 along the outside of the assembly such that when the shape memory alloy wire 810 is heated so as to induce phase transition and associated dimensional change it will incline the displacement cavity 801 toward a state of reduced volume. The shape memory alloy wire 810 is electrically connected by connector 811 to a programmable pulse generating circuit 812 and a source of electric power 813. Hard stops (not shown) on the limits of the relative positions of the shell 802 and tube 803 define the maximum and minimum volumes of the displacement volume 801.

Operation of both the first and second alternative embodiments of the invention proceed in a manner analogous to that described for the most general embodiment and preferred embodiment of the invention.

In all of the embodiments described above, a shape memory alloy wire acts as an actuator to drive a movable member to increase or decrease the fluid volume in the pump head, and once the wire cools a spring is used to return the movable member back to its original position. Those of reasonable skill in this field will appreciate that a multitude of other biasing means exist, one or more of which can be used in place of or in addition to the spring. In fact, a shape memory alloy can be constructed in such a way that it drives the movable member in both directions to act as both an actuator and a return biasing element. For example, the shape memory alloy can be coiled much like a spring to drive the movable member in one direction when heated and in the other direction when cooled.

A first alternative embodiment of a pulse generating circuit is diagrammed schematically in FIG. 9 and is comprised of a 200 milliamp-hour lithium-manganese dioxide primary battery 901, a DC to DC converter 902, a capacitor 903, a low-resistance field effect transistor switch 904, a programmable digital timing circuit 905, an inductor 906 and a diode 908. The shape memory alloy wire is indicated in FIG. 9 symbolically as a resistor 907. The objective of this embodiment of a pulse generating circuit is that the pulses of power delivered to the shape memory alloy wire 907 can be of a higher voltage, and thus higher current, than that associated with the preferred embodiment of a pulse generating circuit diagrammed in FIG. 4 and described previously. A high voltage, high current power pulse has the advantage that it can actuate the circuit in a shorter more efficient time period. Additionally, the alternative embodiment of a pulse generating circuit allows the useful life of the battery 901 to be extended to a lower voltage and can prevent other circuitry powered by the battery from resetting when the battery voltage droops as is likely to happen in the preferred embodiment. The battery 901 and capacitor 903 are electrically connected to each other in parallel through the DC to DC converter 902. The capacitor 903 is further connected to the shape memory alloy wire 907 through the transistor switch 904. The programmable timing circuit 905, also powered by the battery 901 sends a gating signal to the transistor switch 904 as programmed by the user in accordance with their pumping requirements. During the period for which the transistor switch 904 is open, the DC to DC converter 902 draws energy from the battery 901 and stores it in the capacitor 903. Use of the DC to DC converter 902 allows the voltage of the capacitor 903 to be charged to a significantly higher value than that associated with the battery 901 and to be charged to the same voltage throughout the life of the battery 901 regardless of the battery voltage. It is intended that the transistor switch 904 may be modulated to send an overall energy pulse as a single pulse or as a sequence of discrete smaller pulses. It is intended that these smaller pulses may be sequenced so as to tailor a custom profile for the overall energy pulse. The custom profile would ensure optimal energy delivery to the shape memory alloy without exceeding its fusing characteristics. The inclusion of the inductor 906 and diode 908 allows current to continue to flow through the shape memory alloy wire 907 after the transistor switch 904 is opened when the pulse is modulated. This allows further control of the energy delivered to the shape memory alloy.

Various references, publications, provisional and non-provisional United States patent applications, and/or United States patents, have been identified herein, each of which is incorporated herein in its entirety by this reference. Various aspects and features of the present invention have been explained or described in relation to beliefs or theories or underlying assumptions, although it will be understood that the invention is not bound to any particular belief or theory or underlying assumption. Various modifications, processes, as well as numerous structures to which the present invention may be applicable will be readily apparent to those of skill in the art to which the present invention is directed, upon review of the specification. Although the various aspects and features of the present invention have been described with respect to various embodiments and specific examples herein, it will be understood that the invention is entitled to protection within the full scope of the appended claims.

What is claimed is:

1. A device for pumping a predetermined volume of fluid comprising:

a cavity operably associated with an inlet and an outlet, the inlet of a construction sufficient for operable communication with a source of fluid, the cavity at least partially defined by a resilient housing;

an inlet check valve operably associated with the inlet and an outlet check valve operably associated with the outlet;

a member operably associated with the resilient housing, the member disposed in a first position by way of a biasing force and moveable therefrom to a second position, the member sufficient to fully compress the resilient housing when in one of the first position and the second position, and sufficient to fully decompress the resilient housing when in a different one of the first position and the second position;

a biasing element operably associated with the member and of a construction sufficient to provide the biasing force;

an actuator comprising a shape memory alloy, the actuator operably associated with the member and of a construction sufficient to move the member from the first position to the second position when the shape memory alloy undergoes a dimensional change relative to an original condition thereof, and sufficient to move the member from the second position to the first position when the shape memory alloy returns toward the original condition;

wherein, when the inlet is in operable communication with the source of fluid, the cavity is empty of the predetermined volume of fluid when the resilient housing is fully compressed and the cavity is filled with the predetermined volume of fluid when the resilient housing is fully decompressed.

2. The device of claim 1, wherein, when the inlet is in operable communication with the source of fluid, the cavity is filled with the predetermined volume of fluid when the member is in the first position and empty of the predetermined volume of fluid when the member is in the second position.

3. The device of claim 1, wherein, when the inlet is in operable communication with the source of fluid, the cavity is empty of the predetermined volume of fluid when the member is in the first position and being filled with the predetermined volume of fluid when the member is in the second position.

4. The device of claim 1, wherein the resilient housing comprises a tube.

5. The device of claim 1, wherein the resilient housing comprises a tube, the inlet comprises an inlet end of the tube, and the outlet comprises an outlet end of the tube.

6. The device of claim 1, wherein the resilient housing comprises a diaphragm.

7. The device of claim 1, wherein the resilient housing comprises a diaphragm sealed to a substrate, the inlet is operably associated with the substrate, and the outlet is operably associated with the substrate.

8. The device of claim 1, wherein at least one of the inlet check valve and the outlet check valve comprises an elastomeric valve of a construction sufficient for being press-fit into a corresponding one of the inlet and the outlet.

9. The device of claim 1, wherein at least one of the inlet check valve and the outlet check valve comprises an elastomeric valve of low cracking pressure.

10. The device of claim 1, wherein at least one of the inlet check valve and the outlet check valve comprises an elastomeric valve of a construction sufficient to from a fluid-tight seal in the absence of back pressure.

11. The device of claim 1, wherein the biasing element comprises the shape memory alloy.

12. The device of claim 1, wherein the shape memory alloy is sufficient to move the member in one direction when the shape memory undergoes the dimensional change, and sufficient to move the member in an opposite direction when the shape memory alloy returns toward the original condition.

13. The device of claim 1, wherein the dimensional change is reversible, the member returning to the first position by way of the biasing force when the dimensional change is reversed.

14. The device of claim 1, wherein the dimensional change is repeatable, the member movable from the first position to the second position at least two times.

15. The device of claim 1, wherein a volume of the source of fluid diminishes concomitantly as fluid flows therefrom.

16. The device of claim 1, wherein the fluid is a drug.

17. The device of claim 1, wherein the fluid is insulin.

18. The device of claim 17, the device sufficient to pump the predetermined volume of insulin substantially without damage.

19. The device of claim 17, the device sufficient to pump the predetermined volume of insulin substantially without damage over a period of three days.

20. The device of claim 17, the device sufficient to pump the predetermined volume of insulin up to 3000 times.

21. The device of claim 1, wherein the predetermined volume of fluid is in a range of 0.5 microliter to 5 microliters.

22. The device of claim 1, further comprising a housing for the cavity, the member, and the actuator, the housing of a construction sufficient for wearing by a user.

23. The device of claim 1, further comprising a housing for the cavity, the member, the actuator, the inlet, and the source, the housing of a construction sufficient for wearing by a user.

24. The device of claim 22 or claim 23, the housing comprising an adhesive sufficient for adhesion to the skin of a user.

25. The device of claim 1, further comprising:
   a source of electrical energy operably connected to the shape memory alloy of the actuator; and
   a pulse-generating circuit operably connected to the source of electrical energy.

26. The device of claim 25, wherein the pulse-generating circuit is programmable.

27. The device of claim 25, the pulse-generating circuit comprising:
   a battery, a capacitor, a timing circuit, and a transistor switch, wherein the battery and capacitor are operably connected to each other in parallel, the connector is operably connected to the shape memory alloy of the actuator via the transistor switch, and the timing circuit is operably connected to the battery and the transistor switch.

28. The device of claim 27, wherein the capacitor is of lower equivalent series resistance than the battery.

29. The device of claim 27, wherein, when the transistor switch is closed, electrical energy is provided to the shape memory alloy of the actuator primarily via the capacitor.

30. The device of claim 27, wherein the timing circuit is programmable.

31. The device of claim 25, the pulse-generating circuit comprising:
   a battery, a capacitor, a signal converter, a timing circuit, and a transistor switch, wherein the battery and capacitor are operably connected to each other in parallel via the converter, the capacitor is operably connected to the shape memory alloy of the actuator via the transistor switch, and the timing circuit is operably connected to the battery and the transistor switch.

32. The device of claim 31, wherein the signal converter is sufficient for allowing the capacitor to be charged to an equal or greater extent than the battery.

33. The device of claim 31, wherein the signal converter comprises a DC to DC converter.

34. The device of claim 31, wherein the transistor switch is sufficient for modulation to transmit electrical energy in at least one pulse.

35. The device of claim 31, further comprising an inductor and a diode, wherein the capacitor is operably connected to the shape memory alloy of the actuator via the transistor switch, the inductor, and the diode.

36. The device of claim 35, wherein the inductor and the diode are sufficient to allow electrical energy to flow through the shape memory alloy of the actuator after the transistor switch, modulated to transmit electrical energy in at least one pulse, is open.

37. The device of claim 31, wherein the timing circuit is programmable.

38. A method of pumping a predetermined volume of fluid, comprising:
   providing a cavity operably associated with an inlet and an outlet, the cavity at least partially defined by a resilient housing;
   providing an inlet check valve operably associated with inlet, and an outlet check valve operably associated with the outlet;
   providing a member in a first position under bias via a biasing element;
   providing a shape memory alloy operably associated with the member;
   providing at least one pulse of electricity to the shape memory alloy to move the member to a second position; and
   ceasing the providing of at least one pulse of electricity to the shape memory alloy to return the member to the first position;
   the resilient housing being fully compressed when the member is in one of the first position and the second position, and being fully decompressed the resilient housing when the member is in a different one of the first position and the second position;
   wherein, when the inlet is in operable communication with a source of fluid, the cavity is empty of the predetermined volume of fluid when the resilient housing is fully compressed and the cavity is filled with the predetermined volume of fluid when the resilient housing is fully decompressed.

39. The method of claim 38, further comprising cycling through said providing at least one pulse of electricity to the shape memory alloy and said ceasing the providing of at least one pulse of electricity to the shape memory alloy.

40. The method of claim 38, wherein said providing at least one pulse of electricity to the shape memory alloy and said ceasing the providing of at least one pulse of electricity to the shape memory alloy are programmatically controlled.

41. A method of pumping a predetermined volume of fluid, comprising:
   providing a cavity operably associated with an inlet and an outlet, the cavity at least partially defined by a resilient housing;
   providing an inlet check valve operably associated with the inlet, and an outlet check valve operably associated with the outlet;
   providing a member in a first position under bias via a biasing element;
   providing a shape memory alloy operably associated with the member;
   increasing the temperature of the shape memory alloy to move the member to a second position; and
   after said increasing, decreasing a temperature of the shape memory alloy to return the member to the first position;
   the resilient housing being fully compressed when the member is in one of the first position and the second position, and being fully decompressed the resilient housing when the member is in a different one of the first position and the second position;

wherein, when the inlet is in operable communication with a source of fluid, the cavity is empty of the predetermined volume of fluid when the resilient housing is fully compressed and the cavity is filled with the predetermined volume of fluid when the resilient housing of fully decompressed.

42. The method of claim 41, wherein said increasing the temperature of the shape memory alloy comprises providing at least one pulse of electricity.

43. The method of claim 42, wherein said decreasing the temperature of the shape memory alloy comprises ceasing the providing of at least one pulse of electricity.

44. The method of claim 41, further comprising cycling through said increasing the temperature of the shape memory alloy and said decreasing the temperature of the shape memory alloy.

45. The method of claim 41, said increasing the temperature of the shape memory alloy and said decreasing the temperature of the shape memory alloy are programmatically controlled.

46. The device of any of claims 1 and 23, further comprising the source of fluid.

47. The method of any of claims 38 and 41, further comprising providing the source of fluid.

48. The method of any of claims 38 and 42, wherein the at least one pulse comprises more than one pulse.

* * * * *

UNITED STATES PATENT AND TRADEMARK OFFICE
CERTIFICATE OF CORRECTION

PATENT NO. : 6,916,159 B2  Page 1 of 1
DATED : July 12, 2005
INVENTOR(S) : Rush et al.

It is certified that error appears in the above-identified patent and that said Letters Patent is hereby corrected as shown below:

<u>Title page,</u>
Item [62], Related U.S. Application Data, please delete the phrase "provisional application No. 60/424,414, filed on Nov. 6, 2002," (2$^{nd}$ occurrence).

Signed and Sealed this

Twenty-seventh Day of September, 2005

JON W. DUDAS
*Director of the United States Patent and Trademark Office*

UNITED STATES PATENT AND TRADEMARK OFFICE
CERTIFICATE OF CORRECTION

PATENT NO. : 6,916,159 B2 Page 1 of 1
DATED : July 12, 2005
INVENTOR(S) : Rush et al.

It is certified that error appears in the above-identified patent and that said Letters Patent is hereby corrected as shown below:

<u>Title page,</u>
Item [60], Related U.S. Application Data, please delete the phrase "provisional application No. 60/424,414, filed on Nov. 6, 2002,".

This certificate supersedes Certificate of Correction issued September 27, 2005.

Signed and Sealed this

Thirteenth Day of December, 2005

JON W. DUDAS
*Director of the United States Patent and Trademark Office*